US010943302B2

(12) United States Patent
Haile et al.

(10) Patent No.: US 10,943,302 B2
(45) Date of Patent: Mar. 9, 2021

(54) SYSTEMS, METHODS, AND COMPUTER PROGRAM PRODUCTS FOR RISK AND INSURANCE DETERMINATION

(71) Applicant: Mussie Haile, Fairfax, VA (US)

(72) Inventors: Mussie Haile, Fairfax, VA (US);
Filippo Federici Canova, Espoo (FI);
David Z. Gao, Carmel, CA (US)

(73) Assignee: Revolt Cypher, LLC, Fairfax, VA (US)

( * ) Notice: Subject to any disclaimer, the term of this patent is extended or adjusted under 35 U.S.C. 154(b) by 0 days.

(21) Appl. No.: 16/034,357

(22) Filed: Jul. 13, 2018

(65) Prior Publication Data

US 2020/0020038 A1 Jan. 16, 2020

(51) Int. Cl.
| | | |
|---|---|---|
| *G06Q 40/08* | (2012.01) | |
| *G16H 50/30* | (2018.01) | |
| *G16H 10/60* | (2018.01) | |
| *A61B 5/00* | (2006.01) | |
| *H04L 9/06* | (2006.01) | |
| *H04L 9/32* | (2006.01) | |

(52) U.S. Cl.
CPC ........... *G06Q 40/08* (2013.01); *A61B 5/0024* (2013.01); *A61B 5/6802* (2013.01); *G16H 10/60* (2018.01); *G16H 50/30* (2018.01); *H04L 9/0637* (2013.01); *H04L 9/3236* (2013.01); *H04L 2209/38* (2013.01)

(58) Field of Classification Search
CPC ........ G06Q 40/08; G06Q 50/22; G16H 20/30; G06F 3/012
USPC ............................................................ 705/4
See application file for complete search history.

(56) References Cited

U.S. PATENT DOCUMENTS

| | | |
|---|---|---|
| 9,724,042 B1 | 8/2017 | Lodato et al. |
| 2004/0143464 A1 | 7/2004 | Houle |
| 2009/0210256 A1 | 8/2009 | Upadhyayula |
| 2010/0241465 A1* | 9/2010 | Amigo ................... A61B 5/024 705/4 |
| 2016/0147945 A1 | 5/2016 | MacCarthy et al. |

(Continued)

FOREIGN PATENT DOCUMENTS

WO          2017024071           2/2017

OTHER PUBLICATIONS

"score actuarial prize wearables dissertation" (Year: 2018).*
International Search Report from PCT/US2019/041535 dated Oct. 3, 2019.

*Primary Examiner* — Bruce I Ebersman
(74) *Attorney, Agent, or Firm* — Daniel H. Sherr, Esq.

(57) ABSTRACT

The invention enables determining at least one of an insurance risk score or an insurance cost through the steps of (i) receiving from one or more sensors disposed within one or more wearable devices worn by the individual, health parameter data corresponding to one or more states associated with the individual, (ii) validating the received health parameter data based on one or more predefined validation rules, (iii) responsive to validation of the health parameter data, recording said health parameter data and a unique ID associated with the individual in a blockchain, and (iv) retrieving from the blockchain, a plurality of instances of health parameter data associated with the unique ID, and generating based on an analysis of the retrieved plurality of instances of health parameter data, a risk score associated with the individual.

16 Claims, 12 Drawing Sheets

(56) References Cited

U.S. PATENT DOCUMENTS

| | | | |
|---|---|---|---|
| 2016/0378932 A1* | 12/2016 | Sperling | G06F 19/328 |
| | | | 705/3 |
| 2017/0146389 A1* | 5/2017 | Kovacs | G01G 19/50 |
| 2017/0242972 A1 | 8/2017 | Hu et al. | |
| 2017/0316487 A1* | 11/2017 | Mazed | B82Y 5/00 |
| 2017/0337422 A1 | 11/2017 | Hutka et al. | |
| 2018/0204111 A1* | 7/2018 | Zadeh | G06K 9/3233 |
| 2018/0268944 A1* | 9/2018 | Prakash | G16H 80/00 |
| 2020/0151577 A1* | 5/2020 | Ogawa | G06N 5/046 |

\* cited by examiner

Each block contains:

- one or more sets of sensor data (i.e. health parameter data) received from wearable devices
- a unique sensor ID corresponding to each instance of received sensor data / health parameter data
- a unique ID corresponding to a user / individual associated with a wearable device
- biometric data or biometric information acquired from a wearer of a wearable device
- a time stamp associated with received sensor data / health parameter data,
- a device firmware hash value corresponding to each instance of received sensor data / health parameter data and/or
- a unique hash value corresponding to the immediately preceding transaction block within the blockchain ledger BLOCK [i]

FIGURE 5A

| Unique ID | Risk Descriptor(s) / Estimates / Scores | | | | | | |
|---|---|---|---|---|---|---|---|
| | | | | | | | |
| | | | | | | | |

Figure 7

SYSTEMS, METHODS, AND COMPUTER PROGRAM PRODUCTS FOR RISK AND INSURANCE DETERMINATION

FIELD OF THE INVENTION

The disclosure relates to the obtaining and providing of insurance cover. In particular, the invention provides secure and tamper-proof technologies for determining risk profiles, offering insurance coverage and policies specific to the determined risk profiles, and enabling online purchasing of the offered insurance policies.

BACKGROUND

Acquiring life insurance or health insurance can be a confusing process—and can discourage first-time applicants. The difficulty to entry goes against the idea of risk protection that an insurance policy is supposed to represent.

Current processes for obtaining life or health insurance cover involve:
  Completing an application—this usually takes 10 to 20 minutes and involves filling in forms containing general, health related, and beneficiary information
  The medical exam—a full exam is scheduled at a time and place convenient to the applicant. The applicant either needs to visit an examination center, or a nurse is dispatched to the agreed location. The applicant is asked some basic questions, checked for blood pressure, weight, and blood and urine samples are taken. This typically takes more than a half an hour.
  Underwriting—the longest portion of the application involves underwriting. This process is mainly completed by brokers without involving the insuree. The life insurance company reviews the application, accesses the insuree's medical and personal history to assess risk, and assigns a health/rate class. In layman terms that means determining whether the applicant qualifies for insurance and at what cost. The overall process of underwriting can take between 3 to 6 weeks to accomplish unless the applicant opts for a no-exam life insurance policy.
  The decision—once the underwriting is completed the insurer comes back to the insuree with a decision. The insurer can accept the rate that the insuree applied for or offer either a better or worse rate. This depends on several factors such as health, lifestyle, and the medical history of the insuree.

Traditionally, insurance has been an industry with low customer engagement. A 2014 survey by Morgan Stanley and Boston Consulting Group found that consumers interacted less with insurers than with any other industry in the study. Many insurers have limited interaction with a significant portion of the end-consumers because much of their business is intermediated: brokers, for instance, amass an impressive $45 billion in annual compensation from insurers around the world. Furthermore, the slow digitization of the industry has hindered a high frequency of interaction between insurers and insureds. The lack of customer touchpoints has meant that insurers have fewer opportunities to gain insight into customer needs, making it difficult to provide customized solutions.

Additionally, at present, selecting and obtaining an optimal health or life insurance product is a complicated process from both Broker-to-insuree and insuree-to-Broker perspectives. Typically, the process is time-consuming, complicated and tedious—with no guarantee that the insuree with be provided insurance in the end.

Major shifts in client demographics, behaviors, and expectations are underway and will have important ramifications for the insurance landscape. These shifts have been led by Millennials, individuals born roughly between 1980 and 2000, that will constitute half of the global workforce by the end of the decade. In the United States, they already comprise the largest share of the overall population as well as the employed population—at 26% and 34%, respectively. Millennials, whose exposure to digital technology and innovative platforms from an early age have made them the first generation of "digital natives," are beginning to move into their peak earning and spending years and have become an influential segment of the population. Their high expectations for technology-based services, convenience, transparency, speed, regular engagement, and a personalized experience that reflects their needs are defining how products and services are delivered. Their preferences and expectations are a particular challenge for the insurance industry.

Additionally, emerging technologies and innovations are beginning to transform the insurance landscape as they enable new ways to measure, control, and price risk, engage with customers, reduce cost, improve efficiency, and expand insurability. For example, Oscar Health, an insurance startup valued at $2.7 billion, is an example of a company offering policyholders rewards in exchange for exhibiting healthy habits. In 2014, the insurer partnered with Misfit, a company producing wrist-worn sensors, and now encourages participating policyholders to reach daily step goals. If the goals are met 20 times per month, the policyholders are rewarded with a $20 gift card.

There is accordingly a need for solutions and business models is to enable new ways to create, capture, and analyze data valuable to insurance firms. There is additionally a need to automatically, non-intrusively and securely acquire consumer data in real time, and to enable insurers to access such data reliably to calculate and manage risk—and to create opportunities for insurers to underwrite policies that could not traditionally be covered profitably.

SUMMARY

The invention provides solutions relevant for obtaining and providing of insurance cover. In particular, the invention provides secure and tamper-proof technologies for determining risk profiles, offering insurance coverage and policies specific to the determined risk profiles, and enabling online purchasing of the offered insurance policies.

In an embodiment, the invention provides a method for determining at least one of an insurance risk score or an insurance cost, for an individual. The method comprises (i) receiving from one or more sensors disposed within one or more wearable devices worn by the individual, health parameter data corresponding to one or more states associated with the individual, (ii) validating the received health parameter data based on one or more predefined validation rules, (iii) responsive to validation of the health parameter data, recording said health parameter data and a unique ID associated with the individual in a blockchain, and (iv) retrieving from the blockchain, a plurality of instances of health parameter data associated with the unique ID, and generating based on an analysis of the retrieved plurality of instances of health parameter data, a risk score associated with the individual.

The generated risk score may be transmitted to an insurer or insurance broker, and an insurance cost or insurance policy offer may be determined based on the generated risk score.

In an embodiment, the retrieved plurality of instances of health parameter data associated with the unique ID may be transmitted to an insurer or insurance broker. Further, at least one of a risk score associated with the individual, an insurance cost or insurance policy offer may be determined by the insurer or insurance broker based on the transmitted health parameter data associated with the unique ID.

In a particular embodiment the health parameter data transmitted to the insurer or insurance broker is anonymized data that excludes one or both of personal identifiable information and protected health information associated with the individual.

According to certain embodiments of the method, a plurality of insurance costs or insurance policy offers may be determined across a plurality of insurers or insurance brokers based on the health parameter data received from the one or more wearable devices. Said plurality of insurance costs or insurance policy offers may be presented as insurance offers to the individual associated with the unique ID. Each of the plurality of insurance costs or insurance policy offers may be generated based on health parameter data that has been anonymized to exclude one or both of personal identifiable information and protected health information associated with the individual.

In an embodiment of the method, biometric data corresponding to the individual wearing said one or more wearable devices is received from at least one biometric sensor disposed within the one or more wearable devices. The received health parameter data is validated in response to a biometric match decision based on a comparison between the received biometric data and biometric data (i) previously received from at least one biometric sensor disposed within the one or more wearable devices, or (ii) previously received from an individual associated with the wearable device.

Validation of the received health parameter data may include (i) acquiring a first instance of health parameter data from at least one wearable device along with a first set of biometric data captured by the wearable device, (ii) acquiring a second instance of health parameter data from the wearable device along with a second set of biometric data captured by the wearable device (iii) comparing the second set of biometric data with the first set of biometric data to determine a match or a non-match, and (iv) validating the second instance of health parameter data based on the results of the comparison between the first and second set of biometric data.

The invention additionally presents a system for determining at least one of an insurance risk score or an insurance cost, for an individual. The the system comprisEs at least one processor implemented server configured to (i) receive from one or more sensors disposed within one or more wearable devices worn by the individual, health parameter data corresponding to one or more states associated with the individual, (ii) validate the received health parameter data based on one or more predefined validation rules, (iii) responsive to validation of the health parameter data, record said health parameter data and a unique ID associated with the individual in a blockchain, and (iv) retrieve from the blockchain, a plurality of instances of health parameter data associated with the unique ID, and generating based on an analysis of the retrieved plurality of instances of health parameter data, a risk score associated with the individual.

The server may be configured to transmit the generated risk score to an insurer or insurance broker, and receive from the insurer or insurance broker a transmitted insurance cost or insurance policy offer that has been determined based on the generated risk score.

The system may alternatively be configured to transmit to an insurer or insurance broker, the retrieved plurality of instances of health parameter data associated with the unique ID, and receive from the insurer or insurance broker, at least one of a risk score associated with the individual, an insurance cost or insurance policy offer that has been determined by the insurer or insurance broker based on the transmitted health parameter data associated with the unique ID.

In a system embodiment, the server is configured to anonymize health parameter data transmitted to the insurer or insurance broker, prior to such data transmission, wherein anonymizing the health parameter data includes removing, filtering or otherwise excluding one or both of personal identifiable information and protected health information associated with the individual.

In a specific embodiment, the server may be configured to (i) receive a plurality of insurance costs or insurance policy offers that have been determined across a plurality of insurers or insurance brokers based on the health parameter data received from the one or more wearable devices, and (ii) display said plurality of insurance costs or insurance policy offers are presented as insurance offers to the individual associated with the unique ID.

In a system embodiment, each of the plurality of insurance costs or insurance policy offers are generated based on health parameter data that has been anonymized to exclude one or both of personal identifiable information and protected health information associated with the individual.

In another embodiment, the server is configured such that (i) biometric data corresponding to the individual wearing said one or more wearable devices is received from at least one biometric sensor disposed within the one or more wearable devices, and (ii) the received health parameter data is validated in response to a biometric match decision based on a comparison between the received biometric data and biometric data (a) previously received from at least one biometric sensor disposed within the one or more wearable devices, or (b) previously received from an individual associated with the wearable device.

The server may be additionally configured such that validation of the received health parameter data comprises (i) acquiring a first instance of health parameter data from at least one wearable device along with a first set of biometric data captured by the wearable device, (ii) acquiring a second instance of health parameter data from the wearable device along with a second set of biometric data captured by the wearable device (iii) comparing the second set of biometric data with the first set of biometric data to determine a match or a non-match, and (iv) validating the second instance of health parameter data based on the results of the comparison between the first and second set of biometric data.

The invention also provides a computer program product for determining at least one of an insurance risk score or an insurance cost, comprising a non-transitory computer usable medium having computer readable program code embodied therein. The computer readable program code comprises instructions for (i) receiving from one or more sensors disposed within one or more wearable devices worn by the individual, health parameter data corresponding to one or more states associated with the individual, (ii) validating the received health parameter data based on one or more predefined validation rules, (iii) responsive to validation of the health parameter data, recording said health parameter data and a unique ID associated with the individual in a blockchain, and (iv) retrieving from the blockchain, a plurality of instances of health parameter data associated with the unique ID, and generating based on an analysis of the retrieved plurality of instances of health parameter data, a risk score associated with the individual.

DESCRIPTION OF THE ACCOMPANYING DRAWINGS

FIGS. 5A and 5B illustrate exemplary structures for a transaction block within a blockchain in accordance with specific implementations of the present invention.

FIG. 7 illustrates an exemplary data structure that may be used to store risk estimate scores generated based on the method of FIG. 6.

DETAILED DESCRIPTION

The present invention provides secure and tamper-proof technologies for determining risk profiles, offering insurance coverage and policies specific to determined risk profiles, and enabling the online purchase of offered insurance policies. The invention additionally enables the automatic and non-intrusive acquisition of data corresponding to insurees or relating to potential objects sought to be insured—in real time, enabling insurers to access such data reliably to calculate and manage risk and creating opportunities for insurers to underwrite policies that could not traditionally be covered profitably.

Figure 1:
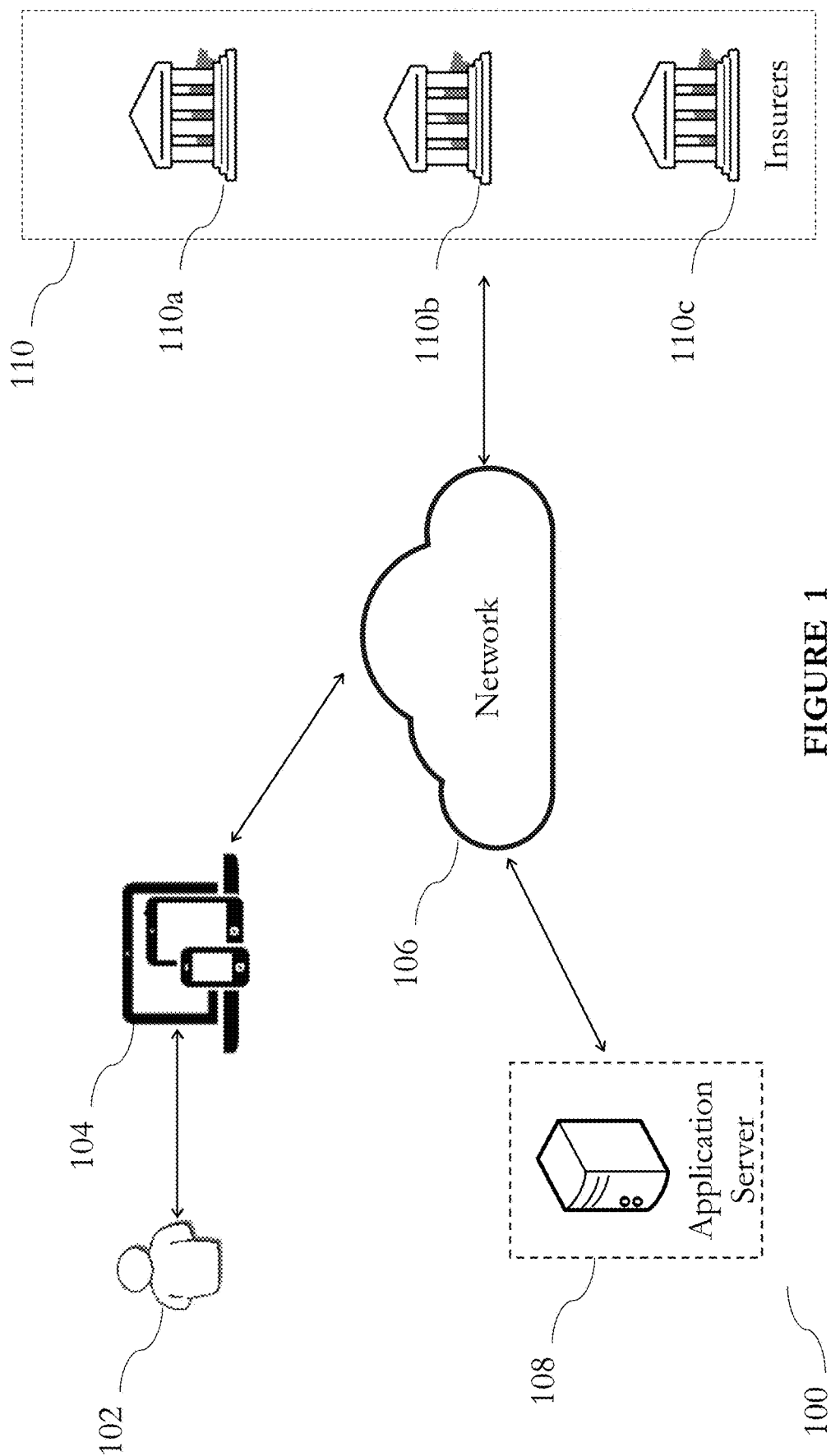
FIG. 1 illustrates a system environment for obtaining insurance online.

FIG. 1 illustrates a system environment for obtaining insurance online. System environment 100 comprises a network-based environment wherein insurers 110 (110a to 110c) provide their insurance policy offerings through online network 106 (which online network 106 may in an embodiment comprise the internet) to application server 108. A user/purchaser 102 may access/view the insurance policy offerings stored on application server 108 through terminal device(s) 104 (which terminal devices may consist of any of a computing device, mobile communication device, or other data processing device capable of network-based communication). In an embodiment, terminal device 104 may have application software provided thereon, which enables the user/purchaser 102 to view insurance policy offerings available on application server 108. The application software may be configured to enable user/purchaser 102 to view or browse through a plurality of insurance policies, review and query features of said policies, and to select one or more policies for further inquiries, or to initiate purchase of a policy by making an online payment to the insurer 110a, 110b, 110c that has offered said policy. However as discussed above, in conventional solutions for purchasing insurance online making an online payment in the system environment 100 would simply act as the commencement of the insurance process—whereafter, the insurer 110a, 110b, 110c offering the selected insurance policy would need to assess the subject matter of the insurance policy (for example in case of health insurance, the insurer would need to carry out various heath checks and tests before finally approving and giving effect to the purchased insurance policy.

Figure 2:
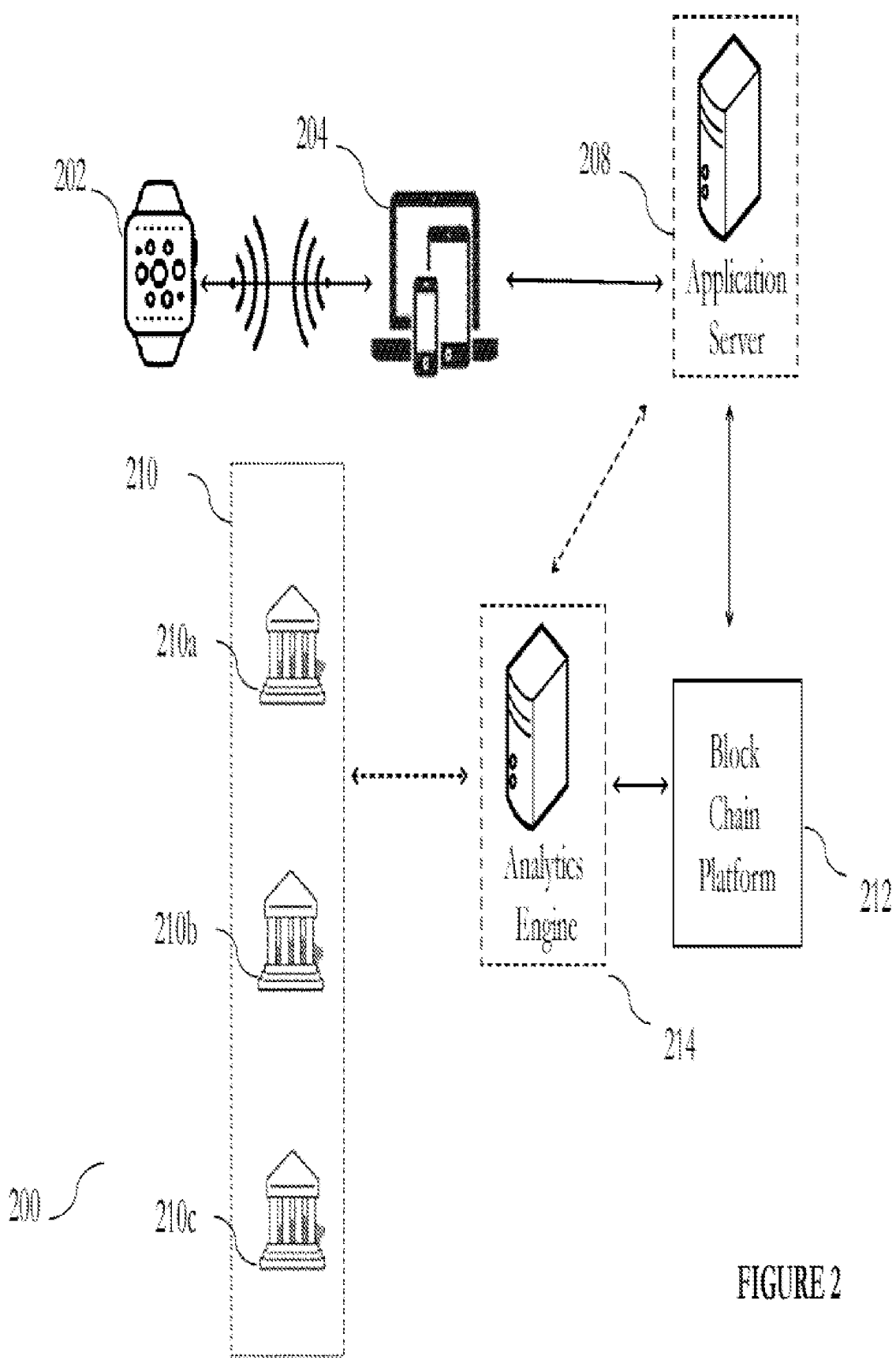
FIGS. 2 and 8 illustrate systems for procuring health insurance in accordance with the teachings of the present invention.

The present invention addresses drawbacks in systems known in the prior art through:
- Use of smart wearable and internet of things (IoT) devices to collect health data
- All collected data may be secured with the insuree's biometrics i.e. finger print or facial recognition
- The collected data is stored in a blockchain distributed ledger and database
- The distributed ledger may be updated with additional health data received from the smart wearable/IOT devices on an incremental basis—which provides a large dataset for analysis and machine learning
- Machine learning algorithms are developed and applied to predict risk factors and recommend suitable insurance providers for the insure
- Insurance providers may access the health data and/or the predicted risk factors and select one or more insurance policy offerings to present to the user/purchaser of insurance
- The health data collected can be presented to the insurance company, in anonymized form without the user/purchaser/insuree's personal identifiable information or protected health information
- The user/purchaser is enabled to purchase an offered insurance policy from the insurer through an electronic contract execution platform
- The user/purchaser may also be provided with a credit reporting site that informs the insuree of his/her risk factor, and offers them better deals from insurers when available FIG. 2 illustrates a system for procuring life or health insurance in accordance with the teachings of the present invention.

FIG. 2 shows a system environment 200 that can be used to implement methods in accordance with the teachings of the present invention. As illustrated, the system environment 200 comprises one or more smart wearable device(s) 202 (for example, fitness trackers, health trackers, smart watches or mobile phones having one or more health data sensors implemented therein) configured to measure user health parameters. Exemplary health parameters may include heart rate, pulse rate, blood pressure, blood analyte parameters, electrocardiogram (ECG) and electroencephalogram (EEG) parameters, skin temperature etc. The smart wearable device(s) may include one or more invasive or non-invasive health data sensors configured to measure health parameters. In certain embodiments, wearable device(s) 202 may additionally include one or more biometric sensors or devices capable of acquiring biometric feature information from the wearer (for example, fingerprint sensors, iris imaging sensors, facial imaging sensors, infra-red based biometric sensors etc). Exemplary wearable devices of the type that may be implemented for the purposes of the present invention include without limitation, Apple Smart Watch™, Fitbit™, Samsung Gear™.

Said smart wearable device(s) 202 may be configured to communicate through a wired or wireless communication protocol with client terminal 204 (for example a computing device, mobile communication device or any data processing device having network communication capabilities)—wherein the health parameter data measured by said wearable device(s) 202 may be communicated to client terminal 204. In an embodiment, client terminal 204 may have implemented thereon, a software application that enables communication of health parameter data from wearable device(s) 202 to client terminal 204. In embodiments of the invention where wearable device(s) 202 are provided with biometric sensors or devices capable of acquiring biometric feature information from the wearer, the acquired biometric information may also be communicated to client terminal 204 along with information associating biometric information obtained from a specific individual/wearer of the a wearable device 202 with the health parameter data corresponding to said specific individual/wearer that have been captured and transmitted by said wearable device(s) 202.

In particular embodiments of the invention, biometric information obtained from a wearer of a wearable device 202 may be used to uniquely ascertain the identity of the individual whose health parameter data are being acquired and transmitted by a wearable device 202. This ensures that health data from a first individual cannot be used to substitute or spoof health data from a second individual, as the identity of each individual whose health parameter data are being measured by wearable device(s) 202 can be accurately verified based on the simultaneously acquired biometric data.

Client terminal 204 is additionally in network communication with application server 208, and health parameter data received from wearable device(s) 202 may be transmitted onward by client terminal 204 to application server 208. Optionally, biometric information associated with said health parameter data that has been received from a wearable device 202 may also be transmitted to application server 208, along with information associating biometric information obtained from a specific individual/wearer of a wearable device 202 with the health parameter data corresponding to said specific individual/wearer that have been captured and transmitted by said wearable device(s) 202.

Application server 208 may be configured to validate the source of health parameter data generated at a wearable device 202—which validation may be based on the biometric data acquired at the wearable device 202. In an embodiment, validation may comprise comparing the received biometric data against one or more instances of biometric data/biometric templates/biometric records stored by application server 208—each of which instances of biometric data/biometric templates/biometric records correspond to a user/individual previously enrolled with application server 208 (for example, a user/individual that has been enrolled as an authorised user/wearer/owner of a specific wearable device or as the authorized user of an electronic account configured to receive health parameter data from one or more wearable devices). In the event the received biometric data matches the biometric data of a user/individual already enrolled with application server 208, the accompanying health parameter data captured by the wearable device can be associate with said enrolled user/individual (i.e. may be treated as health parameter data corresponding to such user/individual). In the event, the received biometric data does not match biometric data of users/individuals enrolled with application server 208, or does not match the biometric data of a user/individual from whom the received health parameter data is supposed or believed to have originated, said health parameter data is treated as invalid data and may be rejected. In another embodiment, validation of health parameter data may comprise (i) acquiring a first instance of health parameter data from a wearable device along with a first set of biometric data corresponding to the wearer of the wearable device (or an individual that has been previously enrolled/registered as a wearer of the wearable device) and associating the first instance of health parameter data and the first set of biometric data with a unique ID corresponding to the wearer of individual wearing the wearable device or with a unique ID corresponding to the wearable device itself, (ii) acquiring a second instance of health parameter data from the wearable device along with a second set of biometric data corresponding to the wearer of the wearable device (iii) comparing the second set of biometric data with the first set of biometric data to determine a match or a non-match, and (iv) validating the second instance of health parameter data based on the results of the comparison between the first and second set of biometric data—i.e. validating the second instance of health parameter data as being data that is valid (i.e. corresponds to the authorized wearer/enrolled wearer of the wearable device) provided the comparison between the first and second set of biometric data results in a match decision. In specific embodiments of the invention, successful validation of the second instance of health parameter data is followed by associating said second instance of health parameter data with the unique ID corresponding to the wearer of individual wearing the wearable device or with the unique ID corresponding to the wearable device itself.

Subject to validation of received health parameter data, said health parameter data are stored in a distributed ledger/blockchain ledger maintained by blockchain platform 212.

It would be understood that implementation of health parameter data storage within blockchain platform 212 secures such data from tampering and malicious attacks—through cryptographic security and through implementation of a decentralized network of peer devices that implement a blockchain ledger.

Briefly, the basis of blockchain technology is the creation of a secure ledger (blockchain ledger) that includes a record of events or transactions that occur on or that are associated with a system. The blockchain ledger forms a database that is stored in a distributed manner across a plurality of peer devices (each acting as a participant database), in a manner that ensures that transactions are verifiable by each peer, and can therefore be verified/validated through a consensus mechanism that ensures transparency and auditability. Additionally, use of the blockchain mechanism ensures that transactions once verified/validated are irrepudiable for the lifetime of the network.

Blockchain technology relies on implementation of one or more smart contracts. In embodiments of the invention, a smart contract comprises executable code that is stored within the blockchain network (for example, on each participant database) and which defines the rules or conditions for verifying/validating transactions and for adding new transactions to the blockchain ledger. The smart contract is stored on each peer device or participant database, and each such device or database executes it and must arrive at the same result for every transaction before such transaction can be added to the blockchain ledger.

Figure 3:
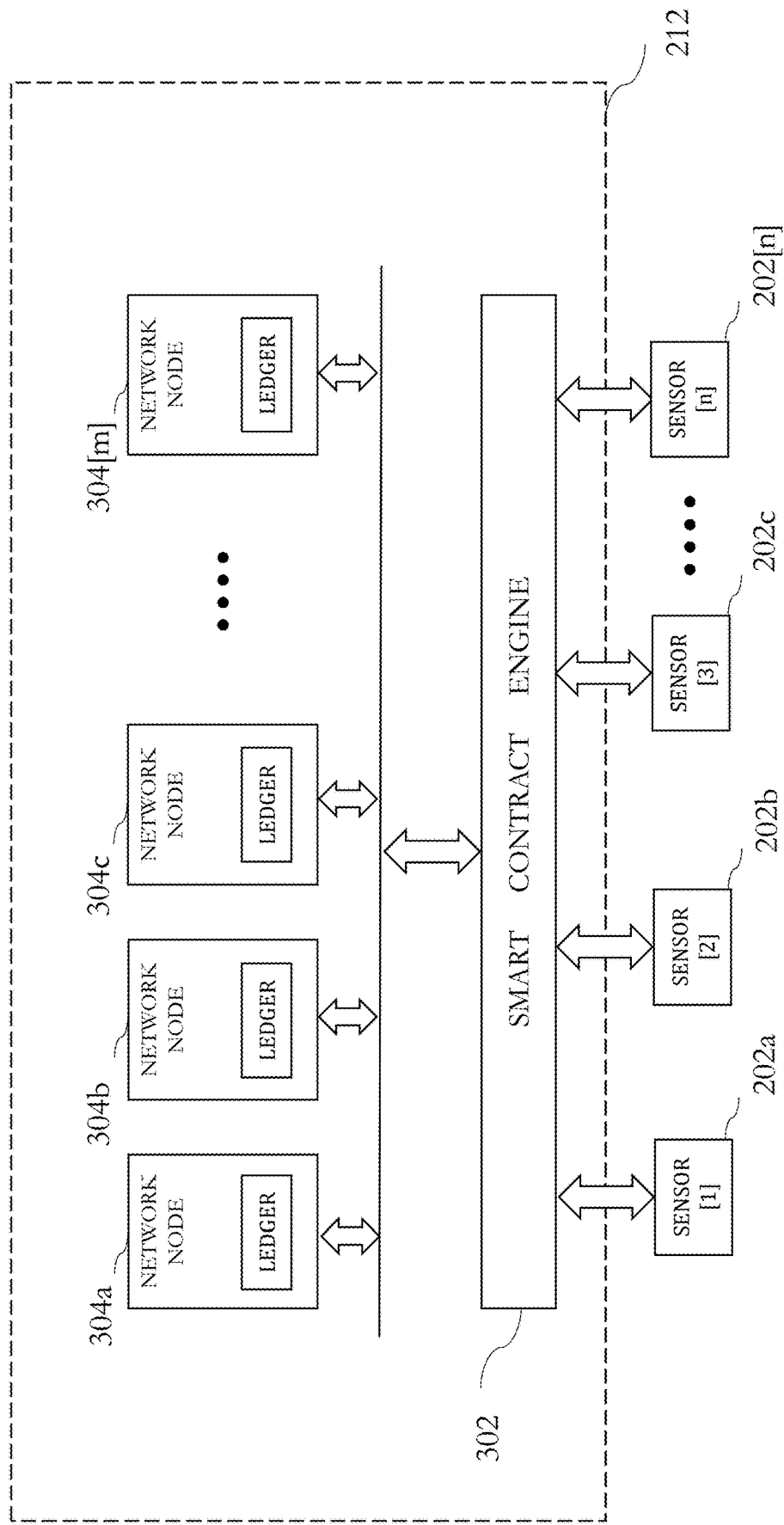
FIG. 3 illustrates an embodiment of the present invention that is based on a blockchain ledger implementation.

FIG. 3 illustrates in more detail exemplary components of blockchain platform 212—configured to implement a blockchain ledger for securing health parameter data in accordance with the teachings of the present invention. As shown in FIG. 3, blockchain platform 212 is configured to receive health parameter data from a plurality of sensors 202a, 202b, 202c upto 202[n]—wherein each sensor may comprise a wearable device 202 of the type illustrated in FIG. 2. Said health parameter data may be received at blockchain platform 212 directly from each sensor—but in preferred embodiments may be received through application server 208. The data from each sensor 202a to 202[n] is received at blockchain platform 212 and may be passed to smart contract engine 302, which smart contract engine 302 is in turn communicably coupled with a plurality of network nodes 304a, 304b, 304c upto 304[m]. Each network node 304a to 304 [m] is configured to operate as a peer device and may store its own copy of the blockchain ledger. It would be understood that the decentralized blockchain platform 212 permits for multiple different configurations including any one or more of the following configurations (i) each network node 304a to 304[m] may be implemented on a respective peer processing device that is external to the sensors 202a to 202[n], or (ii) the smart contract engine 302 may be implemented on a processor that is external to peer devices which are configured to implement one or more network nodes 304a to 304[m], or (iii) each network node may be configured to implement its own copy of the smart contract engine 302, or (iv) a plurality of the network nodes 304a to 304 [m] (and the blockchain ledgers corresponding to said plurality of network nodes) are implemented through a single processing device and/or a single database or single memory repository.

Blockchain platform 212 may be configured such that sensor data (i.e. health parameter data received from each of the sensors 202a to 202[n] is communicated to smart contract engine 302. In particular, secure systems, said sensor data may be cryptographically secured, for example using public-private key cryptography.

Smart contract engine 302 thereafter assesses the received sensor data in accordance with a predefined set of rules or requirements of a predefined smart contract. Subject to received data from a sensor satisfying predefined rules of the smart contract, the transaction is treated as a verified transaction and is consolidated along with one or more other verified transactions within a transaction block. Said transaction block is thereafter added to the blockchain ledger, and appended as the most recent transaction block within the blockchain. In an embodiment of the invention, each block or reading of health parameter data received from wearable devices 202 may be treated and stored as an individual transaction within transaction blocks of the blockchain ledger.

Figure 4:
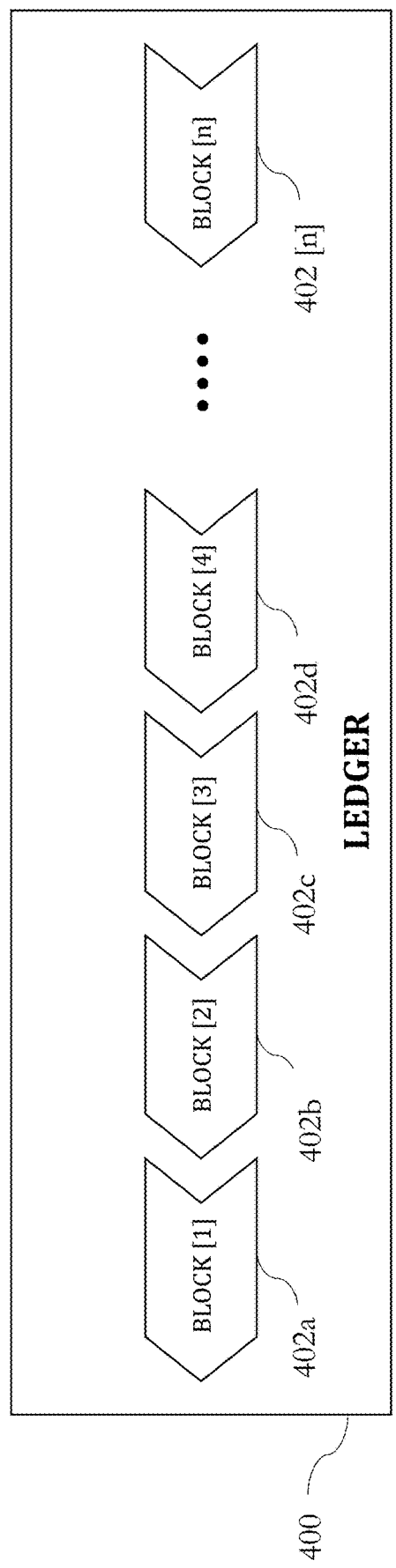
FIG. 4 illustrates an exemplary structure for a blockchain in accordance with the teachings of the present invention.

FIG. 4 illustrates an exemplary blockchain ledger 400 comprising transaction blocks [1] to [n]. Each transaction block is linked to the immediately preceding block in the ledger, for example by ensuring that the header of each transaction block includes information regarding the identity or location of the immediately preceding block in the blockchain—thereby enabling the blockchain ledger to be parsed from the most recently appended transaction block, through each intermediate transaction block and upto the first block in the chain (i.e. upto the root block or the genesis block).

FIG. 5A illustrates an exemplary data structure 500 (block [i]) that may be used to store contents of a transaction block in accordance with a blockchain implementation of the present invention. In the data structure of FIG. 5, a transaction block 500 may include (i) one or more sets of sensor data (i.e. health parameter data) received from wearable devices 202a to 202[n], (ii) a unique sensor ID corresponding to each instance of received sensor data/health parameter data, (iii) a unique ID corresponding to a user/individual associated with the wearable device 202a to 202[n] from which an instance of sensor data/health parameter data has been received, (iv) biometric data or biometric information acquired from a wearer of a wearable device, at the time of (or in chonological proximity to) obtaining of the recorded instance(s) of sensor data/health parameter data, (v) a time stamp associated with each instance of received sensor data/health parameter data, (vi) a device firmware hash value corresponding to each instance of received sensor data/health parameter data—said device firmware hash value comprising the output of a predefined hash function applied to part or whole of device firmware implemented within the sensor responsible for generating the instance of received sensor data/health parameter data, and/or (vii) a unique hash value corresponding to the immediately preceding transaction block within the blockchain ledger. Data structures implementing some or all of the contents of the exemplary data structure of FIG. 5 may be used for the purposes of implementing a blockchain ledger based embodiment of the present invention.

Figure 5B:
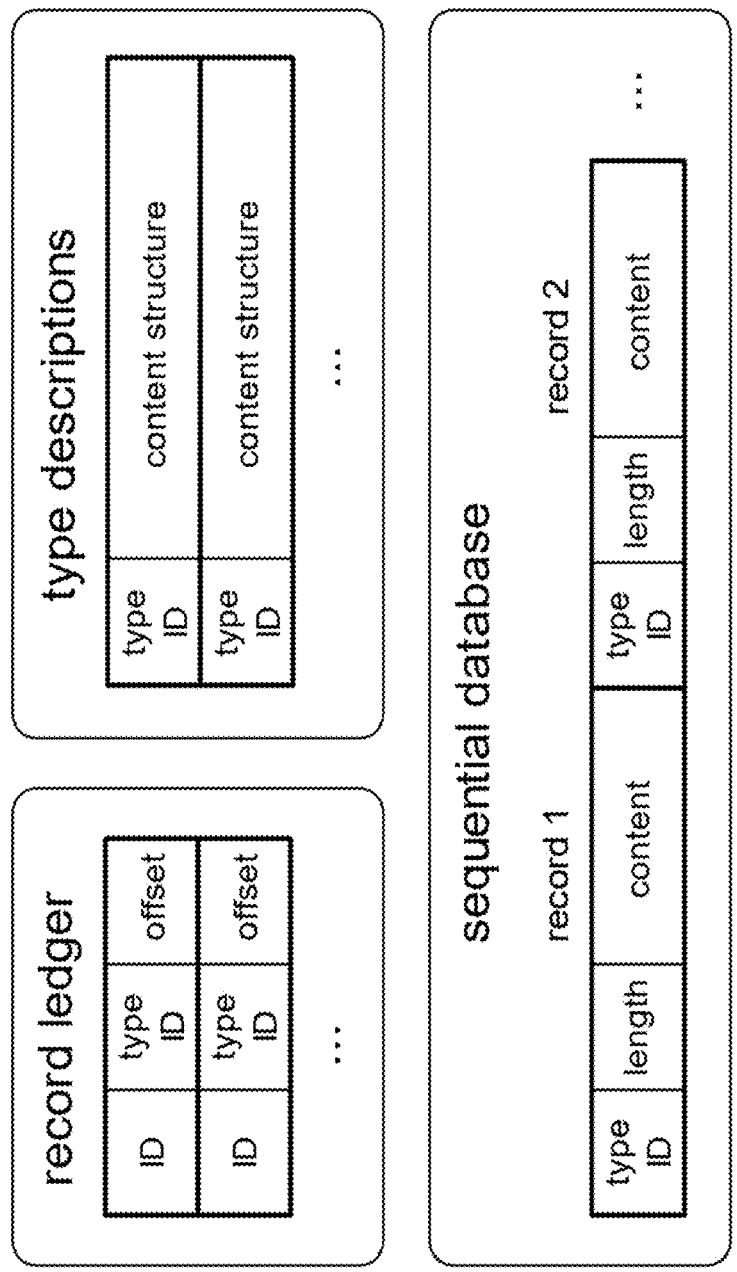

For the purposes of any of transmitting of health parameter data to application server 208, storage of said health parameter data by blockchain platform 212 and/or subsequent analysis of such data by analytics engine 214, the health parameter data may be parsed into a lightweight expandable low metadata format for training, evaluation, and use. The vital sign and health data collected by wearable technology is typically highly heterogeneous. Furthermore, new sensors and types of health parameter datameasurements are continuously introduced into the market. In order to exploit the entire range of possibilities, particular embodiments of the invention implement a flexible, expandable, compact, and accessible data record format. Conventional databases are set up for the purpose of search and retrieval with a heavy emphasis on metadata and identification. However, as the size of these databases increase, it becomes difficult to efficiently perform mathematical operations. Embodiments of the present invention accordingly implement a lightweight format where the metadata is separated from the main data block and where there is no need for blank or null entries. As shown in FIG. 5B, a data record within a sequential database may comprise a type code, a length value and a chunk of variable size content data, as prescribed by the ASN.1 standard. The type-code may be encoded by a single byte, and its value determines the type of content, specified in the data-types collection. The type code can in this embodiment have integer values only between 0 and 255, thus allowing for at most 256 different types.

The succeeding 8 bytes may be interpreted as an unsigned integer, specifying the size L (in bytes) of the data content that follows. The maximum allowed size would in such embodiments be in the region of 107 TB, which should be sufficient in view of anticipated storage requirements, and hardware capabilities. In other embodiments, if it is found to be wasteful to specify 8 bytes for the length of simple data such as integers and floating-point numbers, since their length is already encoded in the type itself. In such cases the 8 bytes for the data length may be omitted to avoid redundancy and save storage space. In certain embodiments, custom data types built from primitives can also have a fixed size that can be inferred from the type descriptor. The last chunk of L bytes of the exemplary data record of FIG. 5B contains the actual data, to be decoded as prescribed by the data-type specified in the first byte of the record.

Referring again to FIG. 2, blockchain platform 212 is communicably coupled with analytics engine 214—wherein analytics engine 214 may be configured to retrieve health parameter data corresponding to a wearer of a wearable device 202 and to estimate risk scores based on an analysis of said health parameter data.

Analytics engine 214 may include one or more neural networks configured to estimate risk scores based on an analysis of health parameter data retrieved from blockchain platform 212. In certain embodiments, the neural network(s) of analytics engine 214 may be trained using one or more machine learning methods—and based on training data sets comprising health parameter data that has been previously received from wearable device(s) 202 and has been validated and stored in blockchain platform 212.

In an exemplary embodiment, training of the neural network(s) may involve application of clustering algorithms (e.g. K-means and self-organizing maps) to reduce the dimensionality of complex data and distribute it among classes. No output is required for these methods since they do not look for an input-output relationship, but rather relationship among the input data itself. These unsupervised machine learning methods provide a fast way of classifying collected data based on similarities, which can be helpful when training supervised machine learning models. Once outputs corresponding to the input data is collected, supervised machine learning can take place. Direct input-output relationships between data of fixed, known size, can be mapped by standard feed-forward neural networks of appropriate depth. In particular embodiments, the neural networks may be trained using back-propagation methods with gradient algorithms—for example, steepest descent and stochastic descent—to find the optimal set of parameters. The accuracy of the model can be improved by training neural networks separately on the clustered data and construct a mixture of expert neural networks. An additional gating neural network may be trained to correlate the similarity of the input data to the clusters and the mixture coefficients of the expert neural network(s).

When the training data/data intended for analysis is data in tabular form (for example matrixes or images), deep convolutional neural networks may be implemented within analytics engine 214. The deep convolutional neural networks may be trained with back-propagation. In particular embodiments, recurrent neural networks are used to process time-series data, such as sounds and heartbeat. Small recurrent neural networks may be trained with back-propagation through time, while more complex ones may be trained with genetic algorithm, due to issues with numerical stability.

In embodiments where data under analysis naturally structured as a relationship table between entities, such data is equivalent to a graph. In such embodiments, the input data consists of the graph node properties or descriptors and the graph topology, while the output is given for one or more of the nodes. Thus, the input and output data do not have a constant, predetermined size, and conventional machine learning methods mentioned hereinabove cannot be applied. In such embodiments, graph neural networks may be implemented—said graph neural networks comprising specific implementations of recurrent neural networks, which have been trained in the manner discussed above.

During the training period, analytics engine 214 retrieves such health parameter data from blockchain platform 212 as may be necessary to machine-learn the relationship between the health parameter data (inputs) and the estimated insurance risk factor(s), policy premium rates, and expected health expenses (output).

During the training period, neural networks and kernel regression models within analytics engine 214 are trained to infer a model for the input-output relationship. Since health parameter data from subject's may initially be scarce, kernel regression may be used to interpolate the complex relationship. As the database of health parameter data grows, neural networks can be trained more properly, resulting in a better model.

The above described configuration and methods for training analytics engine 214 combines multiple neural network technologies to address different parts of the problem where they are more suitable. Recurrent neural networks operate on time-series data, such as the raw output of the vital signs sensors, to compute an intermediate set of descriptors. Additional layers of feed-forward networks then use these descriptors and other customer information to calculate the final output.

Once sufficient training data is processed and the machine learning models exhibit improved accuracy, analytics engine 214 will be able to provide both users and insurance companies with its own estimated risk factors/risk scores, and predicted costs for the insurer. Additionally, by continually training the machine-learned models on new data, analytics engine 214 may be trained to adapt to shifts in market trends over time. Analytics engine 214 may be configured to provide estimated risk factors/risk scores corresponding to a user whose health parameter data has been received through wearable device(s) 202 to one or both of insurers 210 and the user(s) associated with wearable device(s) 202. In some embodiments, said insurers and/or users may receive such data (either through data push or data pull methods) directly from analytics engine 214. In other embodiments, such data may be transmitted to application server 208 for subsequent transmission to or retrieval by said user(s) and/or insurer(s).

Figure 7:
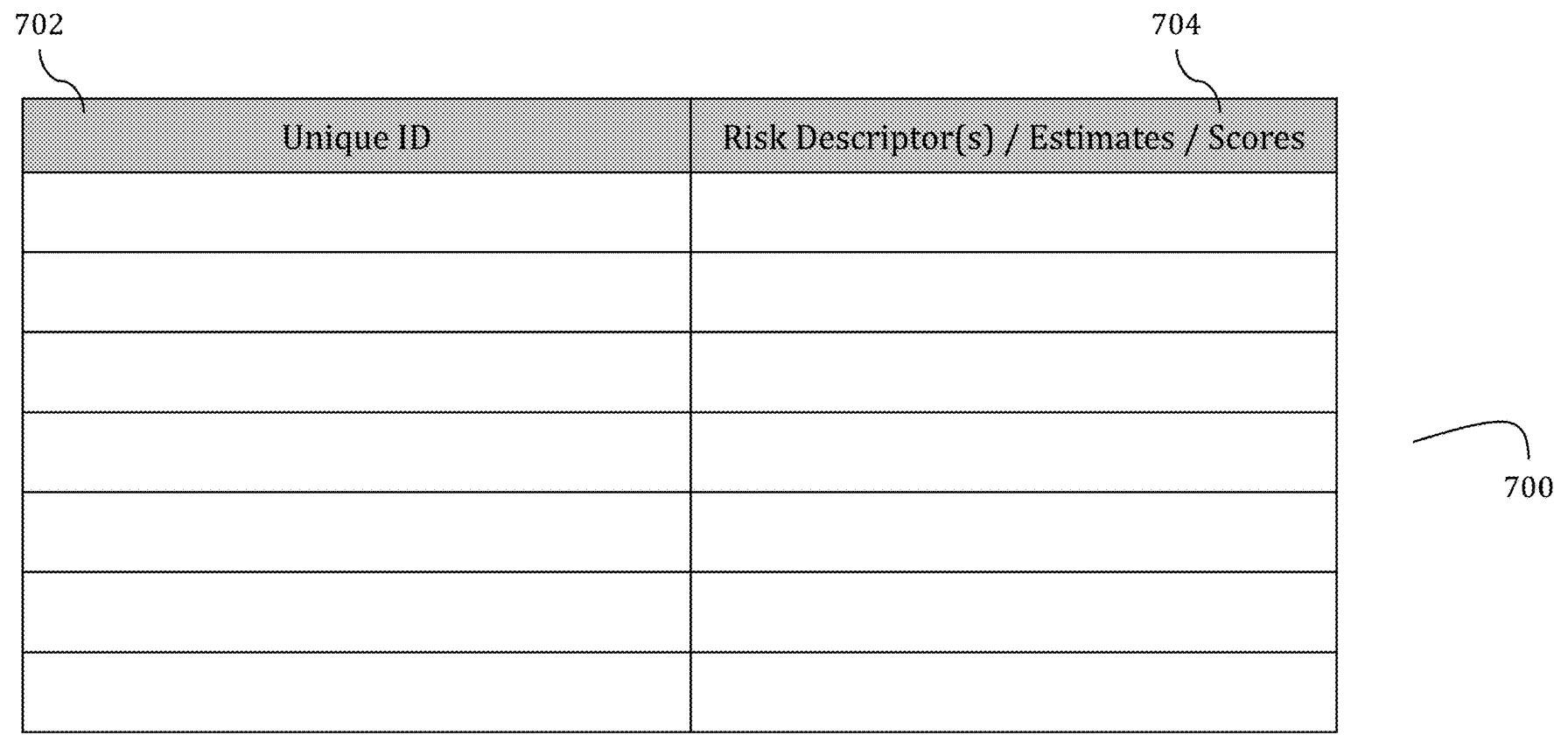

In particular embodiments, the output of analytics engine 214 is one or more risk descriptors—for example risk scores—that are associated with or assigned to an insure/potential insuree/wearer of a wearable device 202. FIG. 7 illustrates an exemplary data record of the type that may be used to retrievably store risk descriptors/risk estimates/risk scores that have been generated by analytics engine 214 based on health parameter data received from one or more wearable device(s) associated with an individual—and which associates said risk descriptors/estimates/scores with a unique ID assigned to said individual. By virtue of associating the risk descriptors with a corresponding unique ID assigned to the individual to whom said risk descriptors correspond—the invention enables both user and insurers to retrieve risk descriptors associated with a specific individual for viewing and providing of insurance offerings.

Yet further, the association between risk descriptors and unique IDs associated with the individual to whom such risk descriptors correspond ensures that risk descriptor data corresponding to individuals can be shared with insurers in an anonymized manner—without sharing any personal identifiable information or protected health information corresponding to such individual. In an embodiment, insurers are provided anonymized access to an individual's risk descriptors, and the system enables insurers to bid/offer insurance policy terms to such individual based on the individual's anonymized information—thereby ensuring that life insurance policy offerings can be provided to individuals solely on the basis of their health data—thereby minimizing the likelihood of prejudice due to any extraneous factors.

Figure 6:
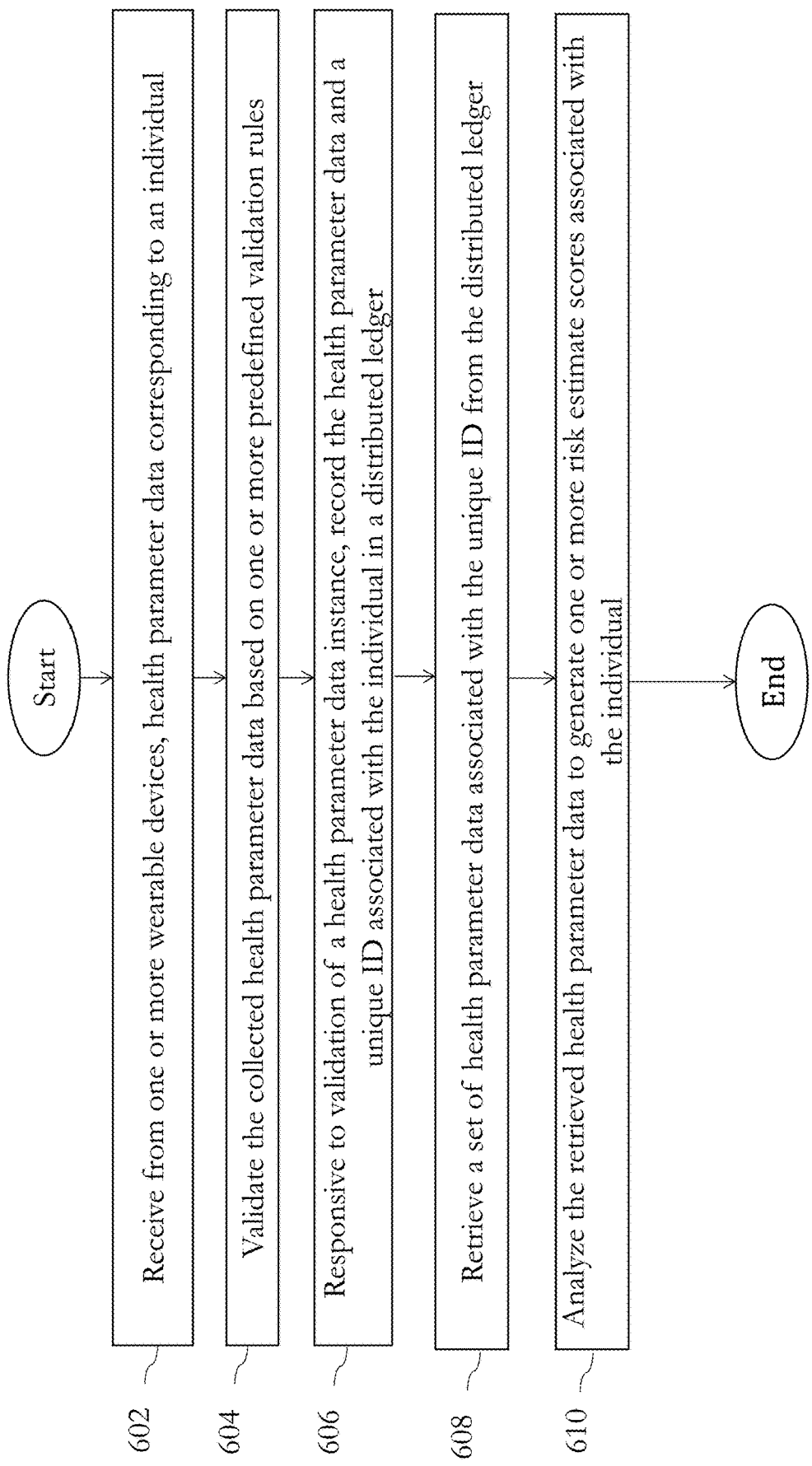
FIGS. 6 and 10 illustrate methods for generating risk estimates and for entering into insurance contracts based on said risk estimates in accordance with the present invention.

FIG. 6 illustrates a method in accordance with the present invention. The method may be implemented in the system environment 200 of FIG. 2.

Step 602 comprises receiving from one or more wearable devices, health parameter data corresponding to an individual subject of insurance. As discussed above, the one or more wearable devices may additionally be configured to obtain biometric data corresponding to the individual. The health parameter data and the biometric data may be transmitted from the one or more wearable devices to an application server.

Step 604 comprises validating the collected health parameter data based on one or more predefined validation rules. In an embodiment of the invention, validation of health parameters data received from a wearable device may include validation based on biometric data received from said wearable device—wherein said validation comprises comparing the received biometric data with at least one biometric template that has been enrolled and associated with a user of the wearable device from which the health parameter data has been received. It would be understood that the validation described in connection with step 606 may include any of the validation steps described in more detail hereinabove.

Step 606 comprises responding to validation of one or more instances of health parameter data received from a wearable device, by recording the health parameter data and a unique ID associated with the individual associated with the wearable device (or associated with the wearable device itself) in a distributed ledger/blockchain. The health parameter data and the unique ID may be associated with each other in the records of the distributed ledger/blockchain.

Step 608 comprises retrieving from the distributed ledger/blockchain, a set of health parameter data associated with the unique ID.

Step 610 comprises analyzing the retrieved health parameter data and generating based on such analysis, one or more risk estimate scores associated with the individual to whom said health parameter data corresponds.

Figure 8:
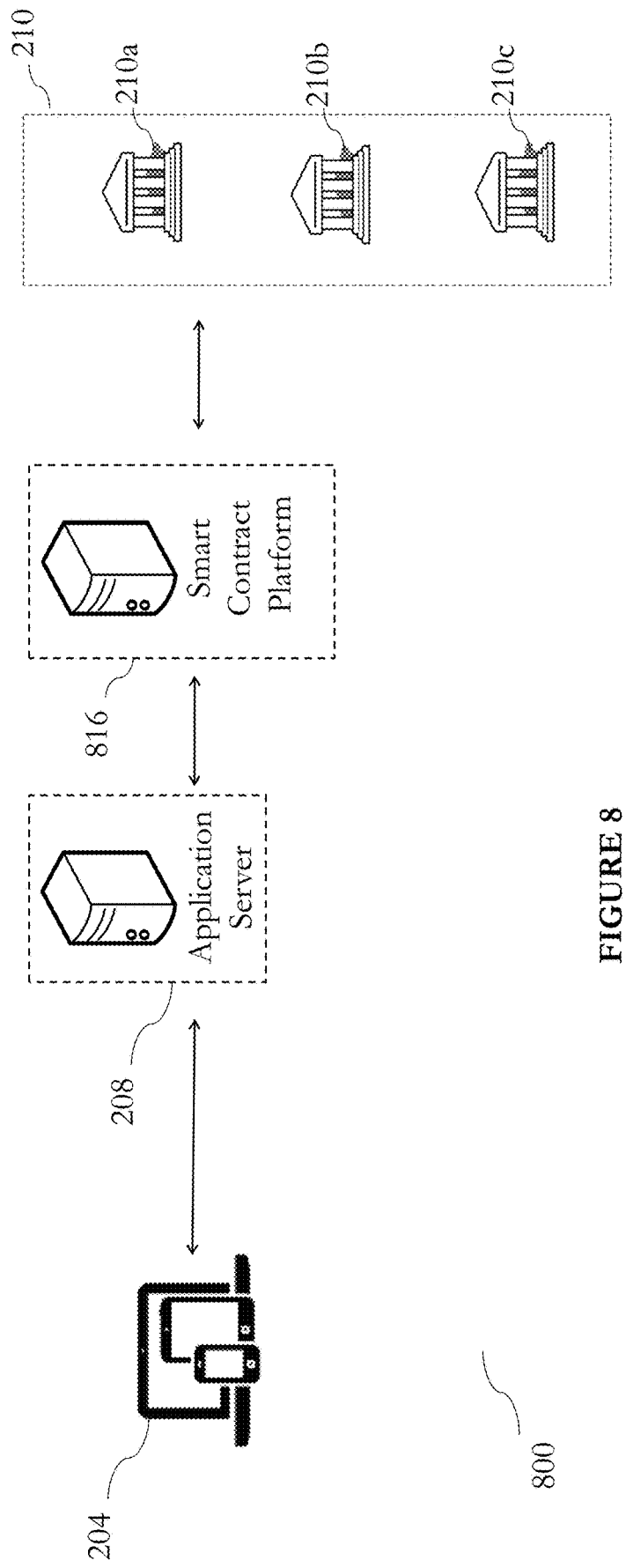

FIG. 8 illustrates a system 800, which enables use of the risk descriptors/risk estimates/risk scores derived in accordance with the teachings of FIGS. 2 and 6—for the purposes of enabling an insurer and potential insuree to electronically conclude an insurance contract for health or life insurance.

As discussed above, based on risk descriptors/risk estimates/risk scores generated by analytics engine 214 of FIG. 2, insurers may offer insurance policies or terms of insurance coverage to an individual through application server 208—which application server 208 may be accessed by client terminal(s) 204 to enable a user to browse or view the offered terms of insurance cover. Thereafter, the user of client terminal(s) 204 may communicate (either directly or through application server 208) with smart contract platform 816. Smart contract platform 816 is an electronic server based platform that enables insurers 210 and a user of client terminal(s) 204 to digitally conclude an insurance contract and to make any premium payments towards said insurance contract, once a user accepts the terms of insurance cover that is offered by one of insurers 210 (210a, 210b, 210c) through application server 208.

Figure 9:
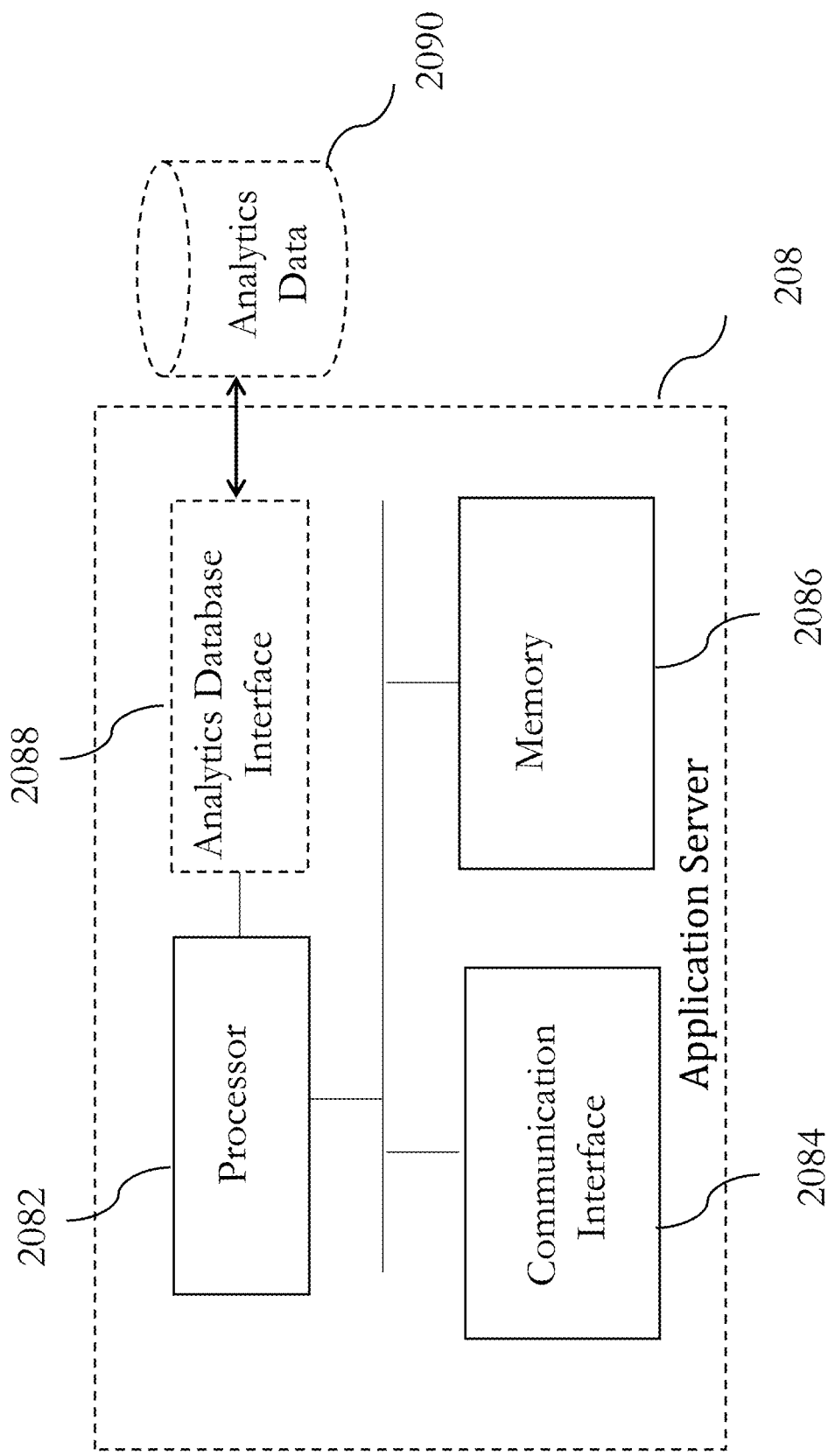
FIG. 9 illustrates an application server configured in accordance with the teachings of the present invention.

FIG. 9 illustrates components of an application server 208 of a kind implemented within the system environment of FIG. 2.

As shown in FIG. 9, application server 208 comprises (i) processor 2082, (ii) communication interface 2084 comprising a processor implemented interface configured for enabling network communication to and from said application server 208, (iii) memory 2086, and (iv) analytics database interface 2088 configured to provide a communication interface between application server 208 and database of analytics data 2090 (which database may be external to application server 208).

Figure 10:
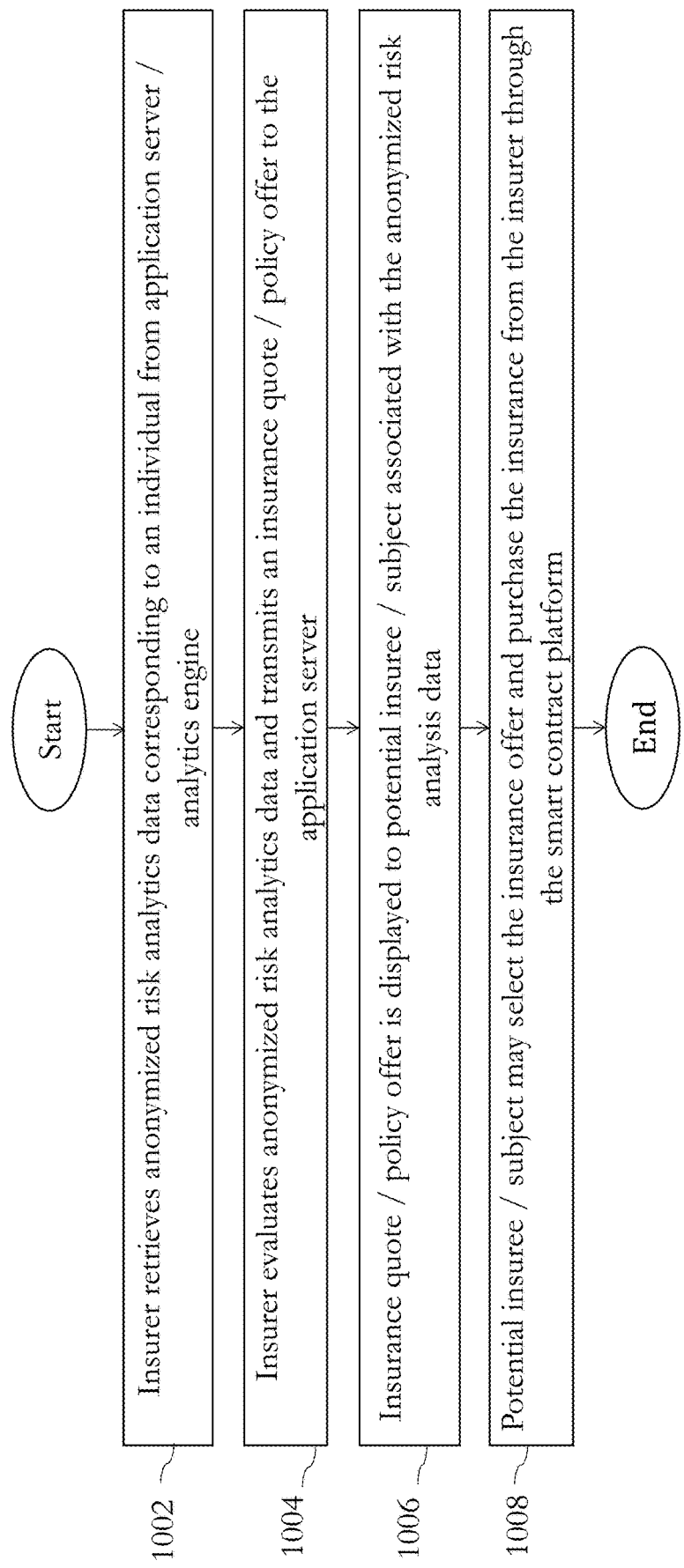

FIG. 10 illustrates a method in accordance with the present invention—wherein the analytics data generated in accordance with the teachings of FIG. 6 may be used for procuring of insurance coverage—for example, health or life insurance coverage.

At step 1002, an insurer retrieves anonymized risk analytics data corresponding to an individual from the application server 208 or analytic engine 214 of FIG. 2. Said risk analytics data may in an embodiment comprise one or more risk descriptors/risk estimates/risk scores corresponding to said individual—that have been derived based on health parameter data received from one or more wearable device(s) that have monitored health data state(s) of said individual.

At step 1004, the insurer evaluates the anonymized risk analytics data and transmits information corresponding to an insurance policy quote and/or information describing an insurance policy offer—to the application server 208.

At step 1006, said insurance policy quote and/or information describing an insurance policy offer is displayed to a potential insuree (in an embodiment, said potential insure is the individual whose health data states have been used to generate the anonymized risk analytics data).

At step 1008, said potential inseree/individual selects the offerend insurance coverage, and purchases the insurance policy from the offering insurer through smart contract platform 816.

Figure 11:
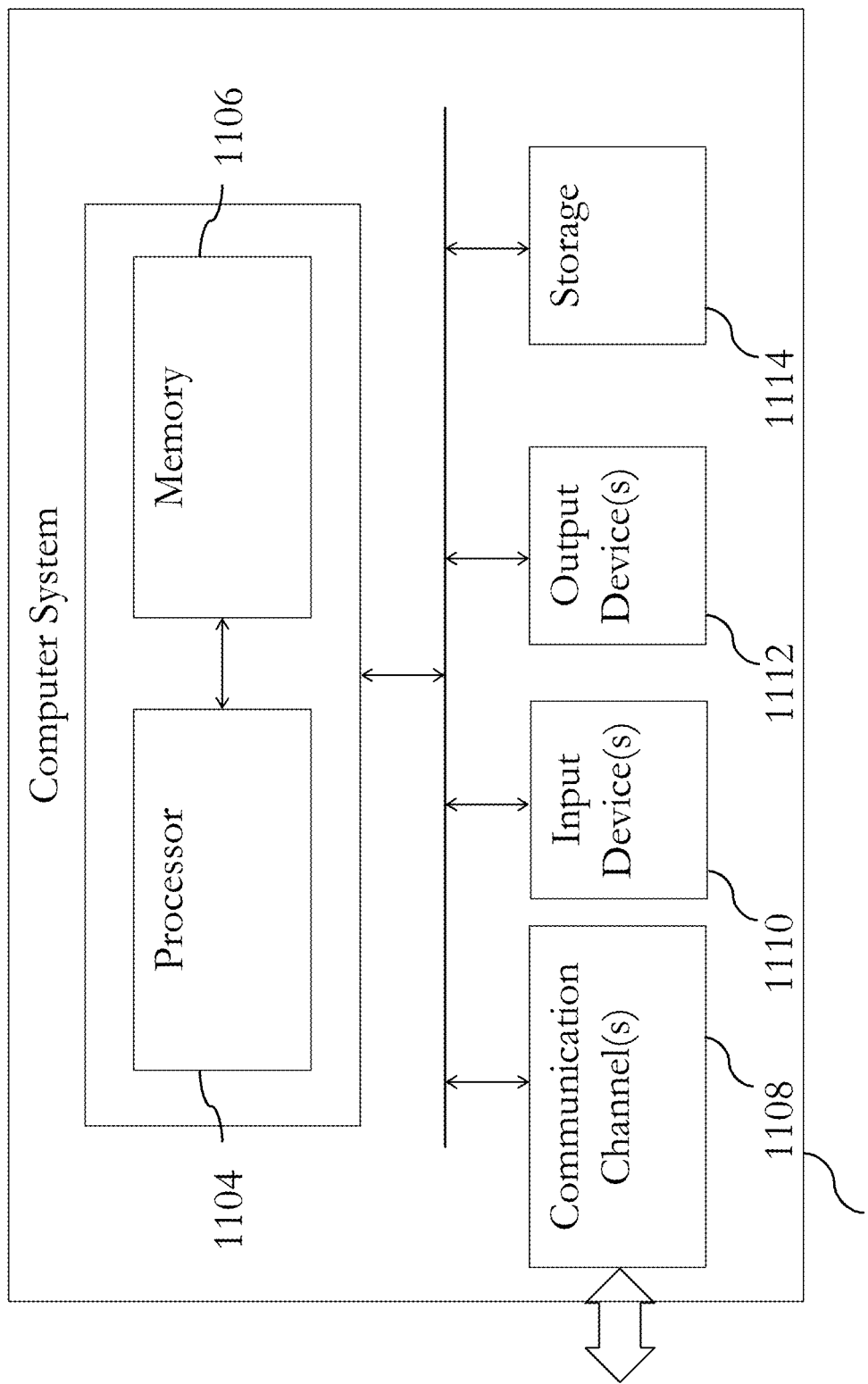
FIG. 11 is an exemplary system that may be configured for implementing the present invention.

FIG. 11 illustrates an exemplary system for implementing the present invention.

The computing system 1102 comprises one or more processors 1104 and at least one memory 1106. Processor 1104 is configured to execute program instructions—and may be a real processor or a virtual processor. It will be understood that computer system 1102 does not suggest any limitation as to scope of use or functionality of described embodiments. The computer system 1102 may include, but is not limited to, one or more of a general-purpose computer, a programmed microprocessor, a micro-controller, an integrated circuit, and other devices or arrangements of devices that are capable of implementing the steps that constitute the method of the present invention. Exemplary embodiments of a system 1102 in accordance with the present invention may include one or more servers, desktops, laptops, tablets, smart phones, mobile phones, mobile communication devices, tablets, phablets and personal digital assistants. In an embodiment of the present invention, the memory 1106 may store software for implementing various embodiments of the present invention. The computer system 1102 may have additional components. For example, the computer system 1102 may include one or more communication channels 1108, one or more input devices 1110, one or more output devices 1112, and storage 1114. An interconnection mechanism (not shown) such as a bus, controller, or network, interconnects the components of the computer system 1102. In various embodiments of the present invention, operating system software (not shown) provides an operating environment for various software executing in the computer system 1102 using a processor 1104, and manages different functionalities of the components of the computer system 1102.

The communication channel(s) 1108 allow communication over a communication medium to various other computing entities. The communication medium provides information such as program instructions, or other data in a communication media. The communication media includes, but is not limited to, wired or wireless methodologies implemented with an electrical, optical, RF, infrared, acoustic, microwave, Bluetooth or other transmission media.

The input device(s) 1110 may include, but is not limited to, a touch screen, a keyboard, mouse, pen, joystick, trackball, a voice device, a scanning device, or any another device that is capable of providing input to the computer system 1102. In an embodiment of the present invention, the input device(s) 1110 may be a sound card or similar device that accepts audio input in analog or digital form. The output device(s) 1112 may include, but not be limited to, a user interface on CRT, LCD, LED display, or any other display associated with any of servers, desktops, laptops, tablets, smart phones, mobile phones, mobile communication devices, tablets, phablets and personal digital assistants, printer, speaker, CD/DVD writer, or any other device that provides output from the computer system 1102.

The storage 1114 may include, but not be limited to, magnetic disks, magnetic tapes, CD-ROMs, CD-RWs, DVDs, any types of computer memory, magnetic stripes, smart cards, printed barcodes or any other transitory or non-transitory medium which can be used to store information and can be accessed by the computer system 1102. In various embodiments of the present invention, the storage 1114 may contain program instructions for implementing any of the described embodiments.

In an embodiment of the present invention, the computer system 1102 is part of a distributed network or a part of a set of available cloud resources.

The present invention may be implemented in numerous ways including as a system, a method, or a computer program product such as a computer readable storage medium or a computer network wherein programming instructions are communicated from a remote location.

The present invention may suitably be embodied as a computer program product for use with the computer system 1102. The method described herein is typically implemented as a computer program product, comprising a set of program instructions that is executed by the computer system 1102 or any other similar device. The set of program instructions may be a series of computer readable codes stored on a tangible medium, such as a computer readable storage medium (storage 1114), for example, diskette, CD-ROM, ROM, flash drives or hard disk, or transmittable to the computer system 1102, via a modem or other interface device, over either a tangible medium, including but not limited to optical or analogue communications channel(s) 1108. The implementation of the invention as a computer program product may be in an intangible form using wireless techniques, including but not limited to microwave, infrared, Bluetooth or other transmission techniques. These instructions can be preloaded into a system or recorded on a storage medium such as a CD-ROM, or made available for downloading over a network such as the Internet or a mobile telephone network. The series of computer readable instructions may embody all or part of the functionality previously described herein.

While the exemplary embodiments of the present invention are described and illustrated herein, it will be appreciated that they are merely illustrative. It will be understood by those skilled in the art that various modifications in form and detail may be made therein without departing from or offending the spirit and scope of the invention as defined by the appended claims. Additionally, the invention illustratively disclose herein suitably may be practiced in the absence of any element which is not specifically disclosed herein—and in a particular embodiment specifically contemplated, is intended to be practiced in the absence of any element which is not specifically disclosed herein.

The invention claimed is:

1. A method performed by at least one processor that determines at least one of an insurance risk score or an insurance cost for an individual, the method comprising:
 receiving from at least one sensor disposed within at least one wearable device worn by the individual health parameter data corresponding to at least one state associated with the individual using the at least one processor, wherein biometric data corresponding to the individual wearing said at least one wearable device is received from at least one biometric sensor disposed within the at least one wearable device;
 validating the received health parameter data based on at least one predefined validation rules using the at least one processor,
  wherein the received health parameter data is validated in response to a biometric match decision based on a comparison between the received biometric data and biometric data that is at least one of previously received from the at least one biometric sensor or previously received from the individual, and
  wherein validation of the received health parameter data comprises at least one of acquiring a first instance of the health parameter data from the at least one wearable device along with a first set of the biometric data captured by the wearable device, acquiring a second instance of the health parameter data from the at least one wearable device along with a second set of the biometric data captured by the at least one wearable device, comparing the second set of the biometric data with the first set of the biometric data to determine a match or a non-match, or validating the second instance of the health parameter data based on the results of the comparison between the first set of biometric data and the second set of the biometric data;
 responsive to validation of the health parameter data, recording said health parameter data and a unique ID associated with the individual in a blockchain using the at least one processor;
 retrieving from the blockchain, a health parameter profile associated with the unique ID using the at least one processor, wherein the health parameter profile comprises the health parameter data; and generating, based on an analysis of the retrieved health parameter profile, a risk score associated with the individual using the at least one processor.

2. The method as claimed in claim 1, wherein:
 the generated risk score is transmitted to at least one of an insurer or an insurance broker using the at least one processor; and
 at least one of an insurance cost or an insurance policy offer is determined based on the generated risk score using the at least one processor.

3. The method as claimed in claim 1, wherein:
 the retrieved health parameter profile associated with the unique ID is transmitted to at least one of an insurer or an insurance broker using the at least one processor; and
 at least one of the risk score associated with the individual, an insurance cost, or an insurance policy offer is determined by at the least one of the insurer or the insurance broker based on the transmitted health parameter profile associated with the unique ID using the at least one processor.

4. The method as claimed in claim 3, wherein the health parameter profile transmitted to at least one of the insurer or the insurance broker is anonymized data that excludes at least one of personal identifiable information or protected health information associated with the individual.

5. The method as claimed in claim 3, wherein:
at least one of an insurance cost or an insurance policy offer is determined from the at least one of the insurer or the insurance broker based on the health parameter data received from the at least one wearable device using the at least one processor; and
said at least one of the insurance cost or the insurance policy offer are presented to the individual associated with the unique ID using the at least one processor.

6. The method as claimed in claim 5, wherein each of the at least one of the insurance cost or the insurance policy offer is generated based on the health parameter data that has been anonymized to exclude at least one of personal identifiable information or protected health information associated with the individual using the at least one processor.

7. A system for determining at least one of an insurance risk score or an insurance cost for an individual, the system comprising at least one processor configured to:
receive from at least one sensor disposed within at least one wearable device worn by the individual health parameter data corresponding to at least one state associated with the individual, wherein biometric data corresponding to the individual wearing said at least one wearable device is received from at least one biometric sensor disposed within the at least one wearable device;
validate the received health parameter data based on at least one predefined validation rule,
wherein the received health parameter data is validated in response to a biometric match decision based on a comparison between the received biometric data and biometric data that is at least one of previously received from the at least one biometric sensor disposed within the one or more wearable devices or previously received from the individual, and
wherein the received health parameter data is validated by at least one of acquiring a first instance of the health parameter data from the at least one wearable device along with a first set of the biometric data captured by the wearable device, acquiring a second instance of the health parameter data from the at least one wearable device along with a second set of the biometric data captured by the at least one wearable device, comparing the second set of the biometric data with the first set of the biometric data to determine a match or a non-match, or validating the second instance of the health parameter data based on the results of the comparison between the first set of the biometric data and the second set of the biometric data;
responsive to validation of the health parameter data, record said health parameter data and a unique ID associated with the individual in a blockchain;
retrieve from the blockchain, a health parameter profile associated with the unique ID, wherein the health parameter profile comprises the health parameter data; and
generating, based on an analysis of the retrieved health parameter profile, a risk score associated with the individual.

8. The system as claimed in claim 7, wherein said at least one processor is configured to:
transmit the generated risk score to at least one of an insurer or an insurance broker; and
receive from the at least one of the insurer or the insurance broker at least one of an insurance cost or an insurance policy offer that has been determined based on the generated risk score.

9. The system as claimed in claim 7, wherein at least one processor is configured to:
transmit to at least one of an insurer or an insurance broker the retrieved health parameter profile associated with the unique ID; and
to receive from the at least one of the insurer or the insurance broker at least one of the risk score associated with the individual, an insurance cost, or an insurance policy offer, wherein the at least one of the risk score, the insurance cost, or the insurance policy offer is determined by the at least one of the insurer or the insurance broker based on the transmitted health parameter profile associated with the unique ID.

10. The system as claimed in claim 8, wherein the at least one processor is configured to anonymize the health parameter profile transmitted to the at least one of the insurer or the insurance broker, wherein anonymizing the health parameter profile comprises at least one of removing, filtering, or excluding at least one of personal identifiable information or protected health information associated with the individual.

11. The system as claimed in claim 9, wherein the at least one processor is configured to:
receive a at least one of an insurance cost or an insurance policy offer that have been determined by at least one of the insurer or the insurance broker based on the health parameter data received from the at least one wearable device; and
display said at least one of the insurance cost or the insurance policy offer to the individual associated with the unique ID.

12. The system as claimed in claim 11, wherein each of the at least one of the insurance cost or the insurance policy offer is generated based on the health parameter data that has been anonymized to exclude at least one of personal identifiable information or protected health information associated with the individual.

13. The system as claimed in claim 7, wherein at least one of said at least one processor is comprised in a server.

14. The system as claimed in claim 7, wherein at least one of said at least one processor is comprised in a portable computing device.

15. The system as claimed in claim 7, wherein at least one of said at least one processor is comprised in at least one of a stationary computing device or a personal computer.

16. A computer program product for determining at least one of an insurance risk score or an insurance cost, comprising a non-transitory computer usable medium having computer readable program code embodied therein, the computer readable program code comprising instructions for:
receiving from at least one sensor disposed within at least one wearable device worn by the individual health parameter data corresponding to at least one state associated with the individual, wherein biometric data corresponding to the individual wearing said at least one wearable device is received from at least one biometric sensor disposed within the at least one wearable device;

validating the received health parameter data based on at least one predefined validation rule,
- wherein the received health parameter data is validated in response to a biometric match decision based on a comparison between the received biometric data and biometric data that is at least one of previously received from the at least one biometric sensor or previously received from the individual, and
- wherein validation of the received health parameter data comprises at least one of acquiring a first instance of the health parameter data from the at least one wearable device along with a first set of the biometric data captured by the wearable device, acquiring a second instance of the health parameter data from the at least one wearable device along with a second set of the biometric data captured by the at least one wearable device, comparing the second set of the biometric data with the first set of the biometric data to determine a match or a non-match, or validating the second instance of the health parameter data based on the results of the comparison between the first set of biometric data and the second set of the biometric data;

responsive to validation of the health parameter data, recording said health parameter data and a unique ID associated with the individual in a blockchain;

retrieving from the blockchain, a health parameter profile associated with the unique ID, wherein the health parameter profile comprises the health parameter data; and generating based on an analysis of the retrieved plurality of instances of health parameter data, a risk score associated with the individual.

\* \* \* \* \*